(12) United States Patent
Moriya

(10) Patent No.: US 8,111,397 B2
(45) Date of Patent: Feb. 7, 2012

(54) PLATE INSPECTION SYSTEM AND PLATE INSPECTION METHOD

(75) Inventor: Norihisa Moriya, Toshima-Ku (JP)

(73) Assignee: Dai Nippon Printing Co., Ltd., Shinjuku-Ku (JP)

( * ) Notice: Subject to any disclaimer, the term of this patent is extended or adjusted under 35 U.S.C. 154(b) by 519 days.

(21) Appl. No.: 12/067,380

(22) PCT Filed: May 14, 2007

(86) PCT No.: PCT/JP2007/059884
§ 371 (c)(1),
(2), (4) Date: Mar. 19, 2008

(87) PCT Pub. No.: WO2007/132818
PCT Pub. Date: Nov. 22, 2007

(65) Prior Publication Data
US 2009/0153849 A1    Jun. 18, 2009

(30) Foreign Application Priority Data

May 15, 2006   (JP) .................................. 2006-135460
Mar. 5, 2007   (JP) .................................. 2007-054669

(51) Int. Cl.
*G01J 4/00*   (2006.01)
(52) U.S. Cl. ....................................................... 356/364
(58) Field of Classification Search .................. 356/364, 356/239.2
See application file for complete search history.

(56) References Cited

U.S. PATENT DOCUMENTS

| | | | |
|---|---|---|---|
| 5,521,705 A * | 5/1996 | Oldenbourg et al. | 356/368 |
| 5,560,864 A | 10/1996 | Goulding | |
| 5,734,158 A | 3/1998 | Nagashima et al. | |
| 5,798,147 A | 8/1998 | Beck et al. | |
| 6,798,511 B1 * | 9/2004 | Zhan et al. | 356/369 |
| 6,842,240 B2 | 1/2005 | Ueta | |
| 7,286,199 B2 | 10/2007 | Moriya | |
| 2005/0213003 A1 * | 9/2005 | Kaneko | 349/114 |

FOREIGN PATENT DOCUMENTS

| | | |
|---|---|---|
| JP | 06-317519 A1 | 11/1994 |
| JP | 07-258638 A1 | 10/1995 |
| JP | 08-292406 A1 | 11/1996 |
| JP | 10-153802 A1 | 6/1998 |
| JP | 10-508882 A1 | 9/1998 |
| JP | 2001-159582 A1 | 6/2001 |
| JP | 2002-148142 A1 | 5/2002 |
| JP | 2003-294578 A1 | 10/2003 |
| JP | 2004-184095 A1 | 7/2004 |
| JP | 2005-003750 A1 | 1/2005 |
| JP | 2005-024920 A1 | 1/2005 |

* cited by examiner

*Primary Examiner* — Tarifur Chowdhury
*Assistant Examiner* — Abdullahi Nur
(74) *Attorney, Agent, or Firm* — Burr & Brown

(57) ABSTRACT

A plate inspection system and a plate inspection method with which irregularities in phase difference caused in a retardation layer can be efficiently detected. The inspection system is for inspecting a plate to be inspected having a retardation layer. The plate inspection system comprises a polarized-light source for irradiating a polarized light and an observation-side polarizer placed on the observation side. In the inspection system, a plate to be inspected is placed between the polarized-light source and the observation-side polarizer so that the plate to be inspected is irradiated with polarized light from the polarized-light source. The position of at least the observation-side polarizer or the plate to be inspected is changeable relative to the polarized-light source.

31 Claims, 11 Drawing Sheets

PLATE INSPECTION SYSTEM AND PLATE INSPECTION METHOD

BACKGROUND OF THE INVENTION

1. Field of the Invention

The present invention relates to an inspection system for use in the inspection of a plate having a retardation layer and to a method of inspecting such a plate, and particularly to a plate inspection system and a plate inspection method with which irregularities in phase difference caused in a retardation layer can be efficiently detected.

2. Background Art

In recent years, a variety of liquid crystal displays have been brought into practical use. These liquid crystal displays are at a disadvantage in that their viewing angles are narrow as compared with CRT displays. Responsible for this disadvantage is mainly the fact that images displayed on the liquid crystal displays are not seen normally when viewed from oblique directions because of the inversion of contrast that occurs due to leakage of light from those pixels that are supposed to display black. By placing a transparent film that is anisotropic with respect to refractive index (hereinafter referred to as a "retardation film") on the surface of a liquid crystal cell, there can be obtained a liquid crystal display with a wide viewing angle, which an observer can observe an image displayed on it without suffering leakage of light even from oblique directions (e.g., Patent Document 1).

However, such a retardation film has the problem that since it is bonded to the substrate of a liquid crystal cell with a pressure-sensitive adhesive in the production of a liquid crystal display, the final thickness of the liquid crystal display inevitably gets greater, especially when a laminate of two or more retardation films is used. Another problem with the retardation film is that since it is poor in heat resistance and shrinks with time, it undergoes a change in optical properties.

In view of these disadvantages, it has recently been proposed that a retardation layer formed by three-dimensionally cross-liking a liquid crystalline polymer be placed on a layer contained in a liquid crystal cell (e.g., Patent Document 2). Since such a retardation layer can be laminated directly to the substrate of a liquid crystal cell without using a pressure-sensitive adhesive, it makes possible to produce a thinner liquid crystal display with improved reliability. Especially when such a retardation layer is incorporated into a color filter for use in a liquid crystal color display, it can be subjected to micropatterning. The incorporation of the retardation layer into a color filter is thus particularly useful.

Patent Document 1: Japanese Laid-Open Patent Publication No. 153802/1998

Patent Document 2: Japanese Laid-Open Patent Publication No. 003750/2005

SUMMARY OF THE INVENTION

Problems to be Solved by the Invention

However, in a retardation layer incorporated into a color filter, irregularities in phase difference (defects) are caused by various factors, one of which is that, in a retardation layer made from a polymerizable liquid crystalline material, some liquid crystalline molecules are aligned in a direction different from that in which surrounding liquid crystalline molecules are aligned.

In view of this point, the present invention was accomplished. An object of the present invention is to provide a plate inspection system and a plate inspection method with which irregularities in phase difference caused in a retardation layer can be efficiently detected.

Means to Solve the Problems

The present invention is a plate inspection system for use in the inspection of a plate having a retardation layer, comprising a polarized-light source for irradiating a polarized light and an observation-side polarizer placed on the observation side, wherein a plate to be inspected is placed between the polarized-light source and the observation-side polarizer so that the plate to be inspected is irradiated with polarized light from the polarized-light source, and the position of at least the observation-side polarizer or the plate to be inspected is changeable relative to the polarized-light source.

Owing to such structure of the plate inspection system, irregularities in phase difference caused in the retardation layer in the plate to be inspected can be efficiently detected.

The present invention is the plate inspection system, in which the observation-side polarizer or the plate to be inspected is movable in the horizontal direction relative to the polarized-light source.

The present invention is the plate inspection system, in which the observation-side polarizer or the plate to be inspected is movable in the vertical direction relative to the polarized-light source.

The present invention is the plate inspection system, in which the observation-side polarizer or the plate to be inspected is rotatable relative to the polarized-light source.

The present invention is the plate inspection system, in which the polarized-light source is movable in the horizontal direction relative to the observation-side polarizer or the plate to be inspected.

The present invention is the plate inspection system, in which the polarized-light source is movable in the vertical direction relative to the observation-side polarizer or the plate to be inspected.

The present invention is the plate inspection system, in which the polarized-light source is, relative to the observation-side polarizer or the plate to be inspected, rotatable about the axis extending in the direction to the observation side from the polarized-light source, the horizontal axis perpendicular to the direction to the observation side from the polarized-light source, and/or the vertical axis perpendicular to the direction to the observation side from the polarized-light source.

The present invention is the plate inspection system, in which the plate to be inspected is a color filter having a retardation layer.

The present invention is the plate inspection system, in which the polarized-light source comprises a light source and a light-source-side polarizer placed on the plate to be inspected side of the light source.

The present invention is the plate inspection system, in which the light-source-side polarizer in the polarized-light source is rotatable about the normal to the light-source-side polarizer, the axis of rotation.

Owing to such structure of the inspection system, the axis of polarization of the polarized light from the polarized-light source can be rotated freely relative to the plate to be inspected, so that irregularities in phase difference caused in the retardation layer can be efficiently detected.

The present invention is the plate inspection system, in which the intensity of light from the polarized-light source is adjustable.

The present invention is the plate inspection system, in which the observation-side polarizer is fixable to the observer's head.

Owing to such structure of the inspection system, an observer can move freely to change his/her position relative to the color filter while checking irregularities in phase difference in the color filter, so that the irregularities in phase difference can be efficiently detected.

The present invention is the plate inspection system, in which the observation-side polarizer is combined with a holding frame for fixing the observation-side polarizer to the observer's head.

The present invention is the plate inspection system, in which the observation-side polarizer is rotatable about the normal to the observation-side polarizer, the axis of rotation, owing to a screw mechanism made in the holding frame.

Owing to this structure of the inspection system, the observation-side polarizer can be rotated about the normal to the observation-side polarizer, the axis of rotation, so that irregularities in phase difference in the retardation layer can be efficiently detected.

The present invention is the plate inspection system further comprising an observation-side-polarizer holder for replaceably holding the observation-side polarizer, wherein the observation-side polarizer held by the observation-side-polarizer holder is replaceable with another observation-side polarizer having the desired axis of transmission.

Owing to this structure of the inspection system, the relationship between the direction of the axis of transmission of the observation-side polarizer and that of the axis of transmission of the light-source-side polarizer can be changed freely, so that irregularities in phase difference caused in the retardation layer in the plate to be inspected can be efficiently detected.

The present invention is the plate inspection system further comprising a light-source-side-polarizer holder for replaceably holding the light-source-side polarizer, wherein the light-source-side polarizer held by the light-source-side-polarizer holder is replaceable with another light-source-side polarizer having the desired axis of transmission.

Owing to this structure of the inspection system, the relationship between the direction of the axis of transmission of the observation-side polarizer and that of the axis of transmission of the light-source-side polarizer can be changed freely, so that irregularities in phase difference caused in the retardation layer in the plate to be inspected can be efficiently detected.

The present invention is the plate inspection system further comprising a plate mount for holding the plate to be inspected, wherein the position of the plate to be inspected relative to the polarized-light source is changed by the plate mount.

Owing to this structure of the inspection system, the plate to be inspected can be positioned at such a point that irregularities in phase difference in the retardation layer can be clearly recognized, so that the irregularities in phase difference can be efficiently detected.

The present invention is the plate inspection system, in which the plate mount has a horizontally movable part that can be moved in the horizontal direction relative to the plate to be inspected, and a rotary part for holding and rotating the plate to be inspected, placed on the horizontally movable part.

The present invention is the plate inspection system, in which the rotary part has an about-Y-axis rotary part that rotates the plate to be inspected about the axis extending in the direction to the observation side from the polarized-light source, an about-X-axis rotary part that rotates the plate to be inspected about the horizontal axis perpendicular to the direction to the observation side from the polarized-light source, and an about-Z-axis rotary part that rotates the plate to be inspected about the vertical axis perpendicular to the direction to the observation side from the polarized-light source.

The present invention is the plate inspection system, in which the plate mount further has, between the horizontally movable part and the rotary part, a vertically extendable part that can be vertically elongated.

The present invention is the plate inspection system, in which the polarized-light source irradiates polarized light that has been colored in one of the three colors, red (R), green (G), and blue (B).

Owing to this structure of the inspection system, it is possible to find efficiently the color in the color filter at which irregularities in phase difference are caused.

The present invention is the plate inspection system, in which the polarized-light source has a white-light source and a polarized-light-source color filter colored in one of the three colors R, G, and B, placed on the plate to be inspected side of the white-light source, and irradiates polarized light colored in one of the three colors, R, G, and B owing to coloring white light from the white-light source by the polarized-light color filter.

The present invention is the plate inspection system, in which the plate to be inspected is a color filter having multiple red, green and blue pixels, the dominant wavelength of light colored in red by the polarized-light-source color filter in the polarized-light source is substantially the same as the dominant wavelength of the red color of the red pixels in the color filter that is the plate to be inspected, the dominant wavelength of light colored in green by the polarized-light-source color filter in the polarized-light source is substantially the same as the dominant wavelength of the green color of the green pixels in the color filter, and the dominant wavelength of light colored in blue by the polarized-light-source color filter in the polarized-light source is substantially the same as the dominant wavelength of the blue color of the blue pixels in the color filter.

Owing to this structure of the inspection system, it is possible to find more efficiently the color pixels in the color filter at which irregularities in phase difference are caused.

The present invention is the plate inspection system, in which the polarized-light source has a source of red light, a source of green light, and a source of blue light, and the three color-light sources are independently switched on or off.

Owing to this structure of the inspection system, it is possible to find efficiently the color in the color filter at which irregularities in phase difference are caused.

The present invention is the plate inspection system, in which the color-light sources in the polarized-light source are cold cathode fluorescent tubes or LEDs.

The present invention is a plate inspection method for inspecting a plate by the use of an inspection system for use in the inspection of a plate having a retardation layer, comprising a polarized-light source for irradiating a polarized light and an observation-side polarizer placed on the observation side, the method comprising a placement step of placing a plate to be inspected between the polarized-light source and the observation-side polarizer so that the plate to be inspected is irradiated with polarized light from the polarized-light source, and a inspection step of inspecting the plate to be inspected by observing the plate to be inspected through the observation-side polarizer while changing the position of at least the observation-side polarizer or the plate to be inspected relative to the polarized-light source.

Owing to this structure of the inspection system, irregularities in phase difference caused in the retardation layer in the plate to be inspected can be efficiently detected.

The present invention is the plate inspection method, in which the inspection step comprises at least one of the following steps: a horizontal movement step of horizontally moving the position of the plate to be inspected relative to the polarized-light source, a vertical movement step of vertically moving the position of the plate to be inspected relative to the polarized-light source, a about-Y-axis rotation step of rotating the plate to be inspected about the axis extending in the direction to the observation side from the polarized-light source, the about-X-axis rotation step of rotating the plate to be inspected about the horizontal axis perpendicular to the direction to the observation side from the polarized-light source, and a about-Z-axis rotation step of rotating the plate to be inspected about the vertical axis perpendicular to the direction to the observation side from the polarized-light source.

The present invention is the inspection system, in which the color filter has color pixels of at least one of red, green and blue, and the polarized-light source irradiates polarized light having a wavelength substantially the same as the wavelength at which the transmittance of light passing through the color pixels reaches a maximum.

Owing to such structure of the inspection system, polarized light from the polarized-light source efficiently passes through the color pixels in the color filter, so that irregularities in phase difference caused in the color filter can be detected more efficiently.

The present invention is the inspection system, in which the color filter has red, green, and blue pixels, and the polarized-light source irradiates polarized light having wavelengths substantially the same as the wavelengths at which the transmittances of light passing through the red, green, and blue pixels reach a maximum.

The present invention is the inspection system, in which the polarized-light source has LEDs or CCFLs that irradiate light having wavelengths substantially the same as the wavelengths at which the transmittances of light passing through the red, green, and blue pixels reach a maximum.

The present invention is a plate inspection method for inspecting a plate by the use of an inspection system for use in the inspection of a plate composed of a color filter having a retardation layer and color pixels of at least one of red, green and blue, the system comprising a polarized-light source for irradiating a polarized light and an observation-side polarizer placed on the observation side, the method comprising a placement step of placing a plate to be inspected between the polarized-light source and the observation-side polarizer so that the plate to be inspected is irradiated with polarized light from the polarized-light source, and a inspection step of inspecting the plate to be inspected by observing the plate to be inspected through the observation-side polarizer while changing the position of at least the observation-side polarizer or the plate to be inspected relative to the polarized-light source, wherein the wavelength of the polarized light from the polarized-light source is substantially the same as the wavelength at which the transmittance of light passing through the color pixels reaches a maximum.

Owing to this structure of the inspection method, the color filter can be inspected with polarized light that efficiently passes through the color pixels in the color filter. Irregularities in phase difference caused in the color filter can therefore be detected more efficiently.

Effects of the Invention

According to the present invention, by changing, relative to the polarized-light source, the position of at least the observation-side polarizer or the plate to be inspected, irregularities in phase difference caused in the retardation layer in the plate can be efficiently detected.

DETAILED DESCRIPTION OF THE INVENTION

First Embodiment

Figure 1:
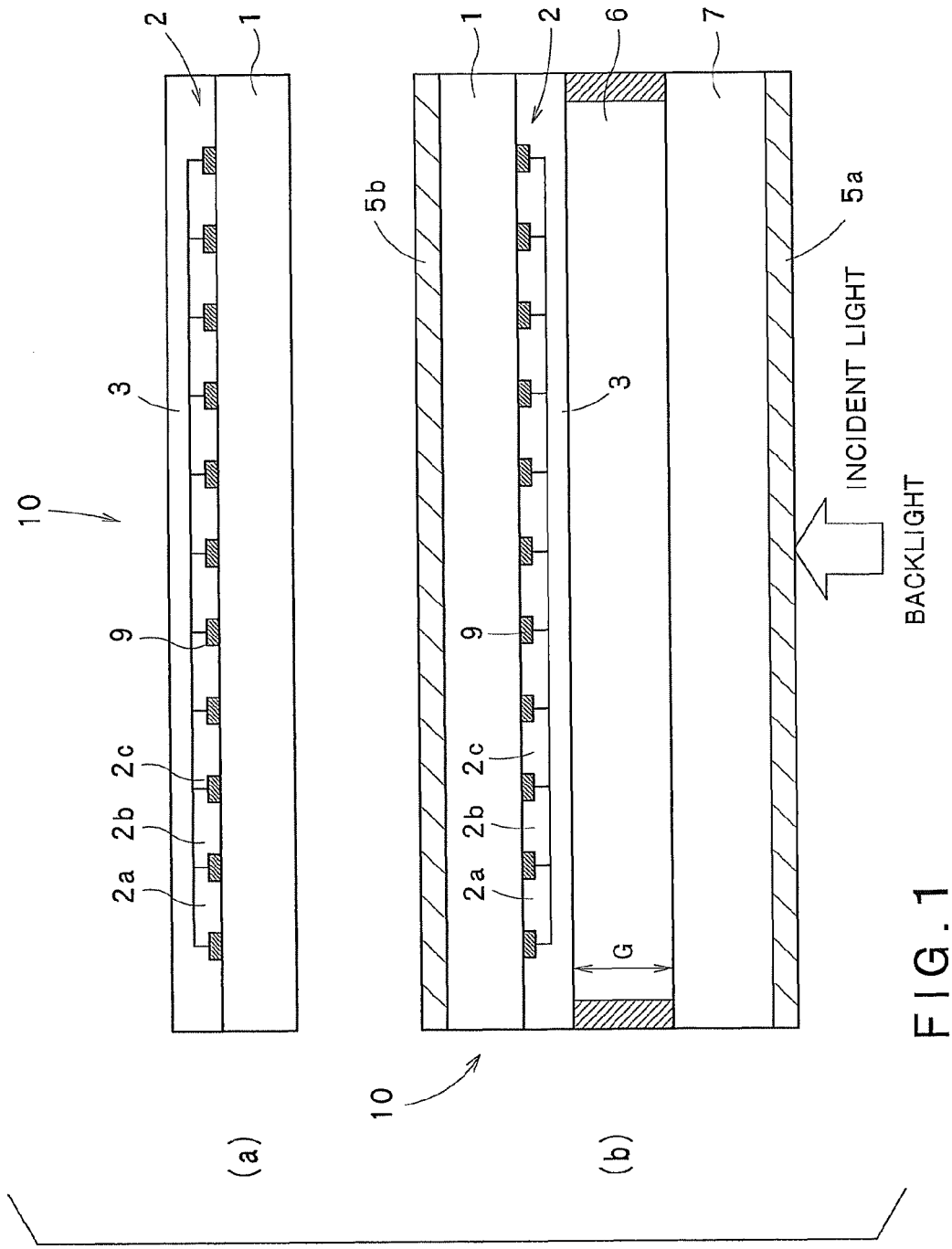
FIG. 1 is a diagrammatic sectional view showing a color filter in the first embodiment of a plate inspection system according to the present invention.

The first embodiment of a plate inspection system according to the present invention will be described hereinafter with reference to the accompanying drawings. FIGS. 1 to 4 show the first embodiment of the present invention.

A plate to be inspected with a plate inspection system according to the present invention will be first described.

For the substrate of a color filter (a plate to be inspected) 10, an object of inspection, plates, sheets, and films made from inorganic transparent materials, and plates, sheets, and films made from organic transparent materials can be used. Inorganic transparent materials are preferred because they are low in thermal expansion and excellent in dimensional stability and show good workability in high-temperature thermal processing. Examples of such inorganic transparent materials include glass, silicon, and quartz. In this embodiment, a glass plate 1 is used as the substrate of a color filter 10, as shown in FIGS. 1(a) and 1(b). The color filter 10 is a member essential to make a liquid crystal display colorific.

The color filter 10, an object of inspection, comprises a glass substrate 1, a coloring layer 2 formed on the glass substrate 1, and a retardation layer 3 formed on the coloring layer 2, as shown in FIG. 1(a). The coloring layer 2 is composed of a plurality of black matrixes 9 that are gridded or in the shape of stripes, and multiple red pixels 2a, green pixels 2b, and blue pixels 2c that are disposed between the black matrixes 9. It is preferable to use non-alkali glass, glass containing no alkali, for the glass substrate 1 of the color filter 10.

The color filter 10 is laminated to a TFT substrate 7 with a certain gap G between them, and this gap G is filled with a liquid crystal 6 for driving, as shown in FIG. 1(b). Further, a light-exiting-side polarizer 5b and a light-entering-side polarizer 5a are laminated to the outer surface of the substrate 1 of the color filter 10 and to that of the TFT substrate 7, respectively, to form a final liquid crystal panel.

A liquid crystalline polymer forming the retardation layer 3 has the property that when the polymer is irradiated with ionizing radiation, its liquid crystalline state is fixed. Specifically, the liquid crystalline polymer is one obtained by three-dimensionally cross-linking a liquid crystalline monomer having unsaturated bonding groups in its molecule, being in the liquid crystalline state, and fixing the three-dimensional cross-linkage with the alignment characteristics of the liquid crystalline structure maintained. Examples of such three-dimensionally cross-linkable liquid crystalline monomers include liquid crystalline monomers disclosed in Japanese Laid-Open Patent Publication No. 258638/1995 and Published Japanese Translation No. 508882/1998 of PCT International Publication for Patent Application.

Next, an inspection system according to the present invention will be described with reference to FIG. 2.

Figure 2:
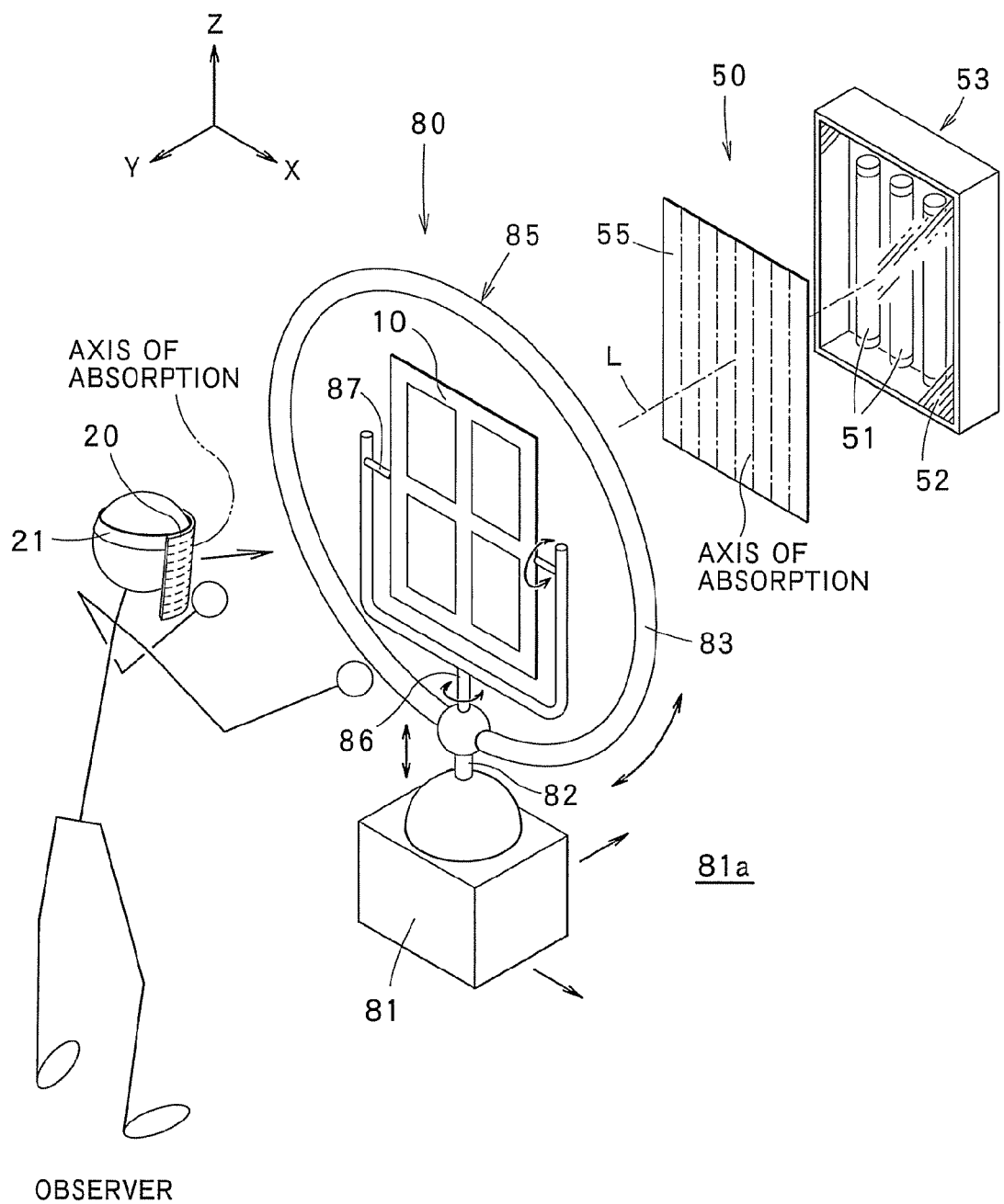
FIG. 2 is a diagrammatic view showing the first embodiment of a plate inspection system according to the present invention.
Figure 3:
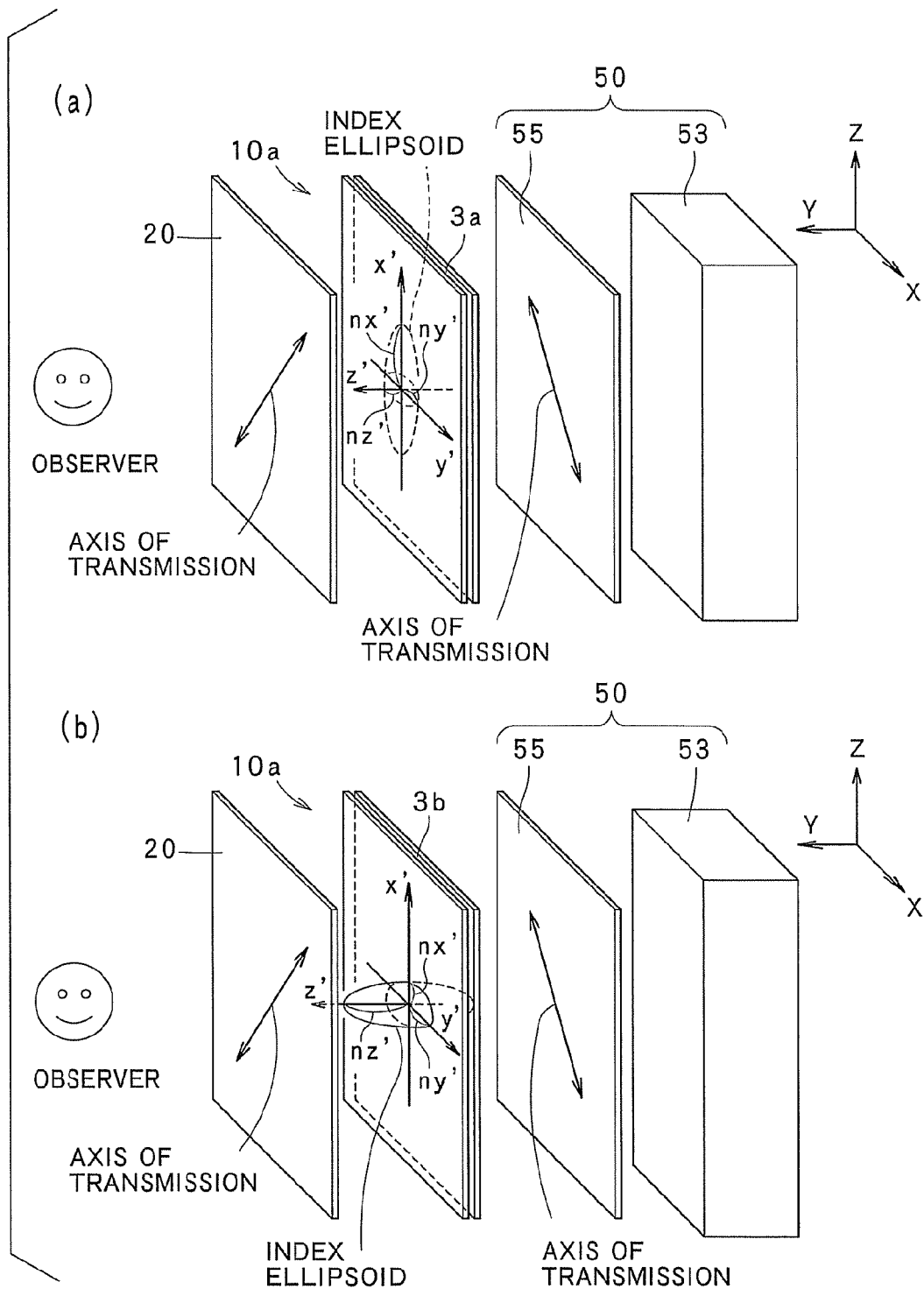
FIG. 3 is a diagrammatic view explaining a method of detecting irregularities in phase difference, for use with the first embodiment of a plate inspection system according to the present invention.

A system for use in the inspection of the color filter 10 comprises a polarized-light source for irradiating a polarized light 50 and an observation-side polarizer 20 placed on the observation side (observer side), as shown in FIG. 2. Between the polarized-light source 50 and the observation-side polarizer 20 is placed a plate mount 80 that holds the color filter 10 so that the color filter 10 is irradiated with polarized light from the polarized-light source 50. In FIG. 2, the direction to the observation side from the polarized-light source 50 is taken as Y-direction. Further, the horizontal direction perpendicular to the direction to the observation side from the polarized-light source 50 is taken as X-direction, and the vertical direction perpendicular to the direction to the observation side from the polarized-light source 50, Z-direction.

The plate mount 80 is composed of a horizontally movable part 81 that can be moved in the horizontal direction (X- and Y-directions) relative to the floor surface (base) 81a, a rotary part 85 for holding and rotating a color filter 10, mounted on the horizontally movable part 81, and a vertically extendable part 82 placed between the horizontally movable part 81 and the rotary part 85, which can be elongated in the vertical (Z-) direction. The rotary part 85 has an about-Y-axis rotary part 83 for rotating the color filter 10 about the axis extending in the Y-direction, an about-X-axis rotary part 87 for rotating the color filter 10 about the axis extending in the X-direction, and an about-Z-rotary part 86 for rotating the color filter 10 about the axis extending in the Z-direction. The plate mount 80 is remote-controlled.

The polarizer 20 placed on the observation side is combined with a holding frame (e.g., a frame for eyeglasses, goggles, or the like) 21 for fixing the observation-side polarizer 20 to the observer's head, so that the observation-side polarizer 20 is fixable to the observers head. Owing to a screw mechanism (not shown in the figure) made in the holding frame 21, the observation-side polarizer 20 can be rotated about the normal to it, the axis or rotation.

The polarized-light source 50 has a light source 53 and a light-source-side polarizer 55 placed on the color filter 10 side of the light source 53, as shown in FIG. 2. The light-source-side polarizer 55 in the polarized-light source 50 is rotatable about the normal to it, the axis of rotation L. The intensity of light from the light source 53 in the polarized-light source 50 is adjustable.

Further, the light source 53 in the polarized-light source 50 has a white-light source 51 and a polarized-light-source color filter 52 placed on the color filter 10 side of the white-light source 51. The polarized-light-source color filter 52 is colored in one of the three colors R, G and B and is replaceable as needed. By selecting the color of the polarized-light-source color filter 52 from the three colors R, G and B, the polarized-light source 50 can irradiate polarized light colored in one of the three colors, R, G, and B owing to coloring white light from the white-light source 51 by the polarized-light color filter 52.

The dominant wavelength of light colored in red by the polarized-light-source color filter 52 in the polarized-light source 50 is substantially the same as the dominant wavelength of the red color of the red pixels 2a in the color filter 10; the dominant wavelength of light colored in green by the polarized-light-source color filter 52 in the polarized-light source 50 is substantially the same as the dominant wavelength of the green color of the green pixels 2b in the color filter 10; and the dominant wavelength of light colored in blue by the polarized-light-source color filter 52 in the polarized-light source 50 is substantially the same as the dominant wavelength of the blue color of the blue pixels 2c in the color filter 10 (see FIG. 1(a) and FIG. 2). For example, that white light is colored in red by the polarized-light-source color filter 52 means that the polarized-light-source color filter 52 absorbs or reflects light contained in white light from the white-light source 51, having wavelengths other than that of red, and transmits only light with the wavelength of red, thereby coloring the white light in red. The dominant wavelength of the red color of the red pixels 2a means the dominant wavelength of red light that passes through the red pixels 2a.

In the above description, the polarized-light source 50 has the white-light source 51 and the polarized-light-source color filter 52 placed on the color filter 10 side of the white-light source 51. However, the polarized-light source 50 is not limited to this. For example, a polarized-light source (not shown in the figure) having a source of red light (not shown in the figure), a source of green light (not shown in the figure), and a source of blue light (not shown in the figure) may also be used. When such a polarized-light source is used, it is preferred that the three color-light sources be independently switched on and off.

For such color-light sources, it is preferable to use a cold cathode fluorescent tube having a red fluorescent substance, a cold cathode fluorescent tube having a green fluorescent substance, and a cold cathode fluorescent tube having a blue fluorescent substance, for instance. In this case, by switching the fluorescent tubes on or off, the color of polarized light can be easily changed. Any light source can be used for the color-light sources as long as it can irradiate light of the desired color, and the use of LEDs of red, green and blue (not shown in the figure) as the color-light sources is also favorable.

The polarized-light source 50 may also be movable in the horizontal direction (the X- and Y-directions) and in the vertical direction (the Z-direction) relative to the observation-side polarizer 20 and the color filter 10. The polarized-light source 50 may also be rotatable, relative to the observation-side polarizer 20 and the color filter 10, about the axis (Y-direction) extending in the direction to the observation side from the polarized-light source 50, the horizontal axis (X-direction) perpendicular to the direction to the observation side from the polarized-light source 50, and/or the vertical axis (Z-direction) perpendicular to the direction to the observation side from the polarized-light source 50.

This embodiment having the above-described structure shows the following actions.

A color filter 10 having no retardation layer 3 is optically isotropic, so that a light source that irradiates unpolarized light can be used for the measurement of the spectral density of the color filter 10 or the detection of defects in the color filter 10. On the other hand, a color filter 10 having a retardation layer 3 has optical anisotropy (phase difference), so that it is necessary to use not isotropic light but polarized light for the detection of defects in the color filter 10. Defects in the color filter 10 can therefore be detected only when the polarized-light source 50 and the observation-side polarizer 20 are used in combination.

Figure 4:
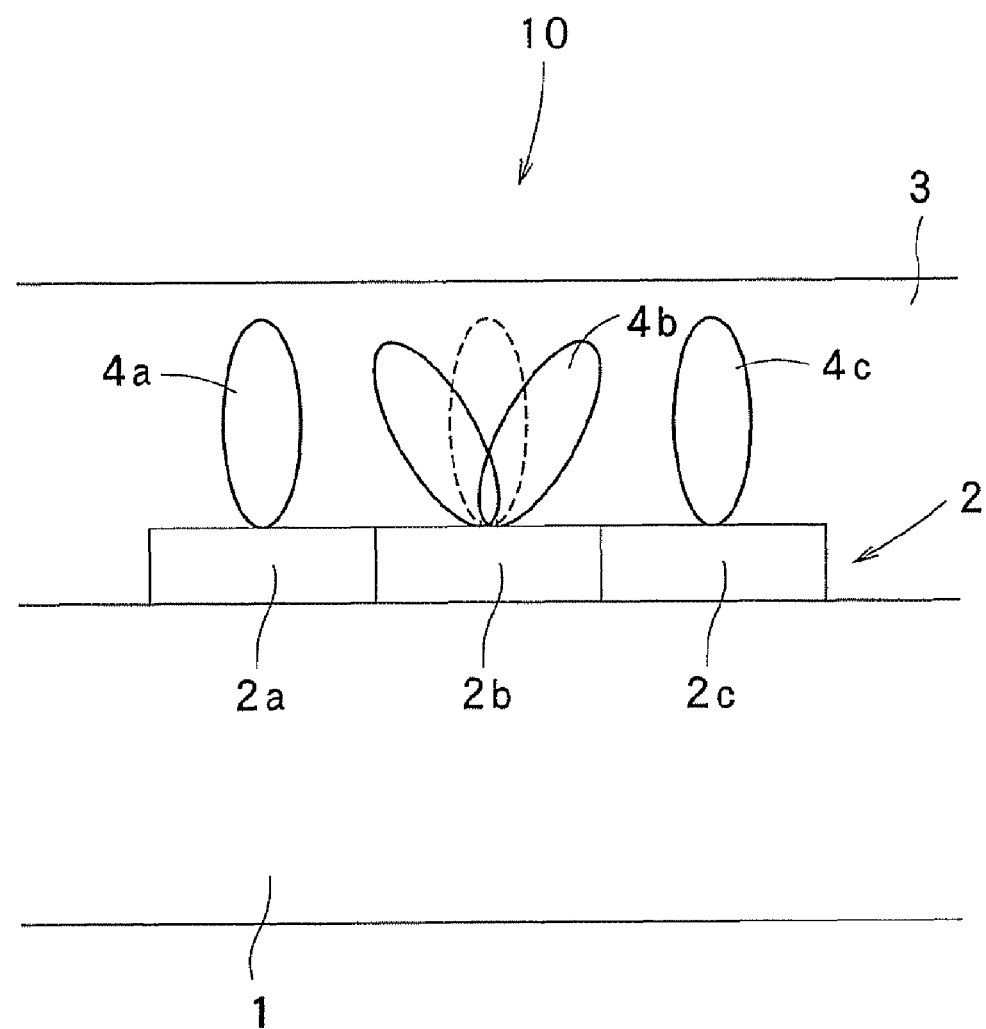
FIG. 4 is a diagrammatic sectional view showing one factor in the causation of irregularities in phase difference that are detected in the first embodiment of a plate inspection system according to the present invention.

In particular, in a color filter 10 having a retardation layer 3 made from a polymerizable liquid crystalline material, irregularities in phase difference (defects) can be caused because of the difference in alignment between liquid crystalline molecules 4b and surrounding liquid crystalline molecules 4a, 4c in the retardation layer 3 (see FIG. 4, the details will be described later). Irregularities in phase difference can also be caused because of the amount of phase difference varying depending on the film thickness distribution and of the surface conditions such as "waviness".

Specific examples of the retardation layer 3 include the following: a retardation layer (positive A plate) with an optic axis in its plane, having positive birefringence anisotropy, its refractive indexes $n_{x'}$, $n_{y'}$, and $n_{z'}$, in the directions of the x'-axis, the y'-axis, and the z'-axis, respectively, being in the relationship $n_{x'} > n_{y'} = n_{z'}$, where the z'-axis is in the direction of the normal to the retardation layer 3, and the x'-axis and the y'-axis perpendicular to the x'-axis are in the plane of the retardation layer 3, as shown in FIGS. 3(a) and 3(b); a retardation layer (negative A plate) with an optic axis in its plane, having negative birefringence anisotropy, its refractive indexes $n_x$, $n_y$, and $n_z$ being in the relationship $n_y > n_z = n_x$; and a retardation layer (positive C plate) with an optic axis in the direction of the normal to it, having positive birefringence anisotropy, its refractive indexes $n_x$, $n_y$, and $n_z$ being in the relationship $n_x = n_y > n_z$; and so forth.

For example, irregularities in phase difference in a color filter 10a having a retardation layer 3 that is a positive A plate 3a (in which the optic axis of an index ellipsoid extends in the direction of the x'-axis of the retardation layer 3) can be efficiently detected when the light-source-side polarizer 55 in the polarized-light source 50 is brought into the state of crossed Nicols with the observation-side polarizer 20 (the state in which the axis of transmission of the light-source-side polarizer 55 and that of the observation-side polarizer 20 are perpendicular to each other) (see FIG. 3(a)).

However, when a color filter 10b having a retardation layer 3b that is a positive C plate 3b (in which the optic axis of the index ellipsoid extends in the direction of the z' axis of the retardation layer 3) is used, almost no phase difference is introduced between polarized light rays that have passed through the positive C plate 3b. For this reason, even if the light-source-side polarizer 55 in the polarized-light source 50 is brought into the state of crossed Nicols with the observation-side polarizer 20, irregularities in phase difference in the color filter 5ob cannot be efficiently detected, and only when the color filter 5ob is rotated by means of the about-X-axis rotary part 87 or the about-Z-axis rotary part 86, the irregularities in phase difference can be detected (see FIG. 2 and FIG. 3(b)).

Therefore, as shown in FIG. 2, by making the light-source-side polarizer 55 in the polarized-light source 50 rotatable about the axis of rotation L that is the normal to the light-source-side polarizer 55, and making the color filter 5ob rotatable by the about-X-axis rotary part 87 or the about-Z-axis rotary part 86, the direction of the axis of transmission of the light-source-side polarizer 55 can be changed freely relative to the observation-side polarizer 20, and irregularities in phase difference in the color filter 10b can be efficiently detected.

Further, as shown in FIG. 2, since the polarizer 20 placed on the observation side is combined with a holding frame 21 for fixing the observation-side polarizer 20 to the observer's head, an observer can fix the observation-side polarizer 20 to his/her head. The observer can therefore move freely in any direction relative to the color filter 10 while checking irregularities in phase difference caused in the color filter 10, so that he/she can efficiently detect the irregularities in phase difference.

Furthermore, the observation-side polarizer 20 is rotatable about the normal to it, the axis of rotation, owing to a screw mechanism made in the holding frame 21, so that the observer can efficiently detect irregularities in phase difference in the color filter 10 without rotating the light-source-side polarizer 55 in the polarized-light source 50.

Furthermore, as shown in FIG. 2, the color filter 10 is held by a rotary part 85 of a plate mount 80, having the above-described about-X-axis rotary part 87 and about-Z-axis rotary part 86 and an about-Y-axis rotary part 85. The rotary part 85 is mounted on a horizontally movable part 81 that can be moved on the floor surface 81a in the horizontal direction. A vertically extendable part 82 that can be vertically elongated is placed between the horizontally movable part 81 and the rotary part 85.

The color filter 10 can therefore be rotated about the X-axis, the Y-axis, and the Z-axis, and moved in the directions of the X-axis, the Y-axis, and the Z-axis, so that the position of the color filter 10 can be changed freely relative to polarized light from the polarized-light source 50. The color filter 10 can thus be positioned at such a point that irregularities in phase difference in the color filter 10 can be clearly recognized, so that the irregularities in phase difference can be efficiently detected.

A color filter 10 produced by laminating, directly to a coloring layer 2, a retardation layer 3 made from a polymerizable liquid crystalline material is readily affected by color pixels, so that irregularities in phase difference tend to be caused in correspondence with the red, green, and blue pixels 2a, 2b, and 2c. For example, in the case where the green pixels 2b are in bad conditions and are not compatible with the retardation layer 3, liquid crystalline molecules 4a and liquid crystalline molecules 4c in the retardation layer 3, situated on the red pixels 2a and the blue pixels 2c, respectively, stand straight in the direction of the normal to the retardation layer 3, but liquid crystalline molecules 4b in the retardation layer 3, situated on the green pixels 2b, tilt. For this reason, irregularities in phase difference are caused only in those portions of the retardation layer 3 that are situated on the green pixels 2b.

By irradiating such a color filter 10 with polarized light colored in one of the three colors R, G and B by a polarized-light-source color filter 52 whose color is properly selected from the three colors, it is possible to find efficiently the color of the color pixels 2a, 2b, 2c at which irregularities in phase difference are caused. For example, even when a color filter 10 in which irregularities in phase difference are caused only at the green pixels 2b, as described above, is irradiated with polarized light colored in red and blue, the polarized light colored in red and blue do not pass through the green pixels 2b at which irregularities in phase difference are caused, so that an observer recognizes no abnormality. On the other had, when this color filter 10 is irradiated with polarized light colored in green, this polarized light passes through the green pixels 2b at which irregularities in phase difference are caused, so that an observer can detect the irregularities in phase difference at the green pixels 2b. The observer can thus efficiently know that irregularities in phase difference are caused at the green pixels 2b.

The dominant wavelength of light colored in red by the polarized-light-source color filter 52 in the polarized-light source 50 is substantially the same as the dominant wavelength of the red color of the red color pixels 2a in the color filter 10; the dominant wavelength of light colored in green by the polarized-light-source color filter 52 in the polarized-light source 50 is substantially the same as the dominant wavelength of the green color of the green color pixels 2b in the color filter 10; and the dominant wavelength of light colored in blue by the polarized-light-source color filter 52 in the polarized-light source 50 is substantially the same as the dominant wavelength of the blue color of the blue color pixels 2c in the color filter 10. The polarized light, therefore, efficiently passes through the objective color pixels (e.g., the green pixels 2b) and is efficiently intercepted by the non-objective color pixels (e.g., the red pixels 2a and the blue pixels 2c), so that irregularities in phase difference in the color filter 10 can be detected more efficiently.

Second Embodiment

Next, the second embodiment of the present invention will be described with reference to FIGS. 5 to 7. In the second embodiment shown in FIG. 5, an observation-side polarizer 20 and a light-source-side polarizer 55 are replaceably held by a holder 60. The holder 60 serves as both an observation-side polarizer holder and a light-source-side polarizer holder.

Further, as shown in FIGS. 6(a) and 6(b), the holder 60 is, on its internal surface, provided with a first guide rail 71 for guiding the observation-side polarizer 20 and a second guide rail 72 for guiding the light-source-side polarizer 55. Between the first guide rail 71 and the second guide rail 72 is placed a third guide rail 73 for guiding and holding a color filter 10. A light source 53 is attached to the second guide rail 72, on the side opposite to the third guide rail 73. Except for these points, the structure of the second embodiment is nearly the same as that of the first embodiment shown in FIGS. 1 to 4. FIG. 6(a) is a cross-sectional view of the holder 60 holing the observation-side polarizer 20, the color filter 10, and the light-source-side polarizer 55, and FIG. 6(b) is a plane view of the holder 60 holding the observation-side polarizer 20, the color filter 10, and the light-source-side polarizer 55.

Figure 5:
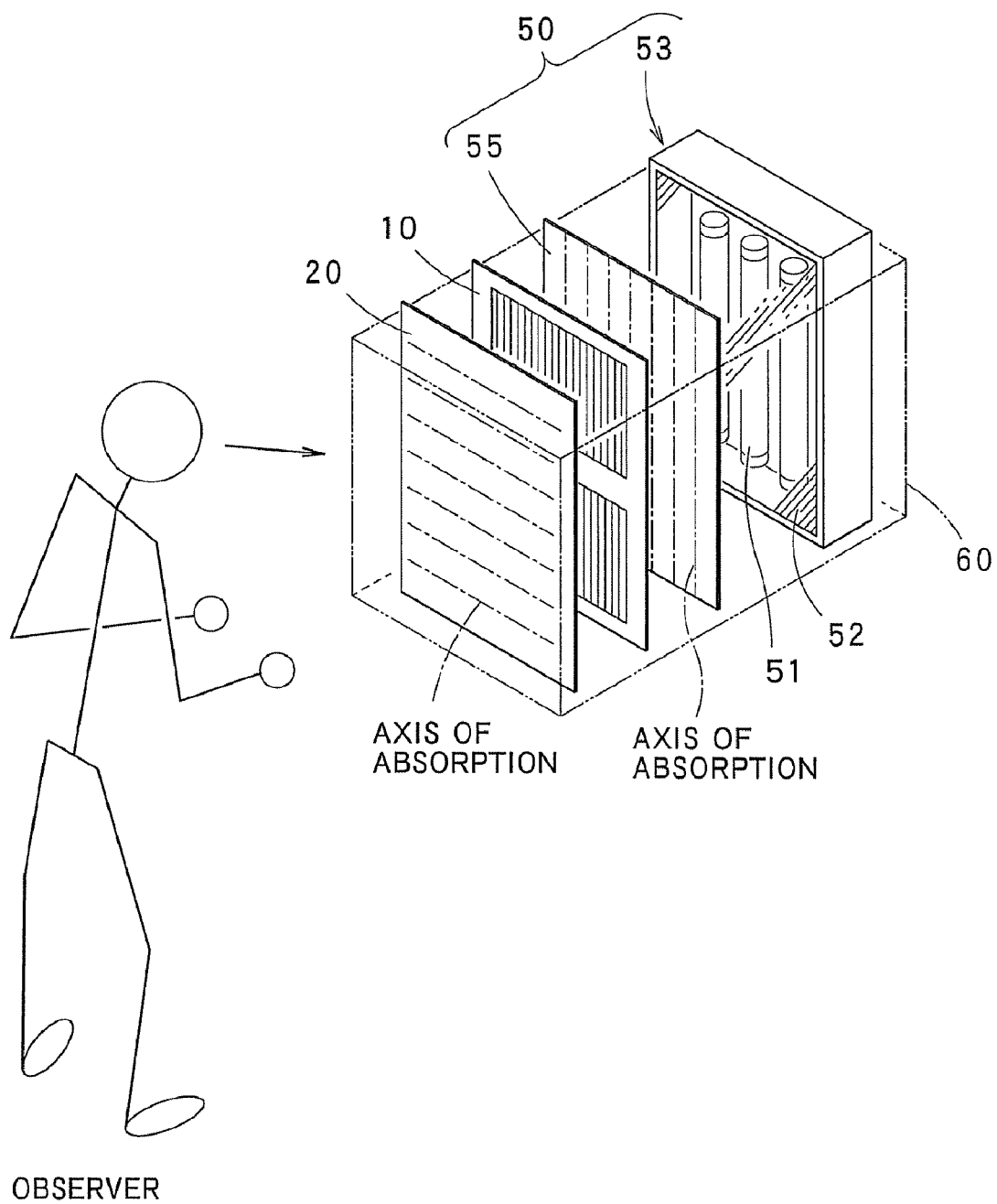
FIG. 5 is a diagrammatic view showing the second embodiment of a plate inspection system according to the present invention.
Figure 6:
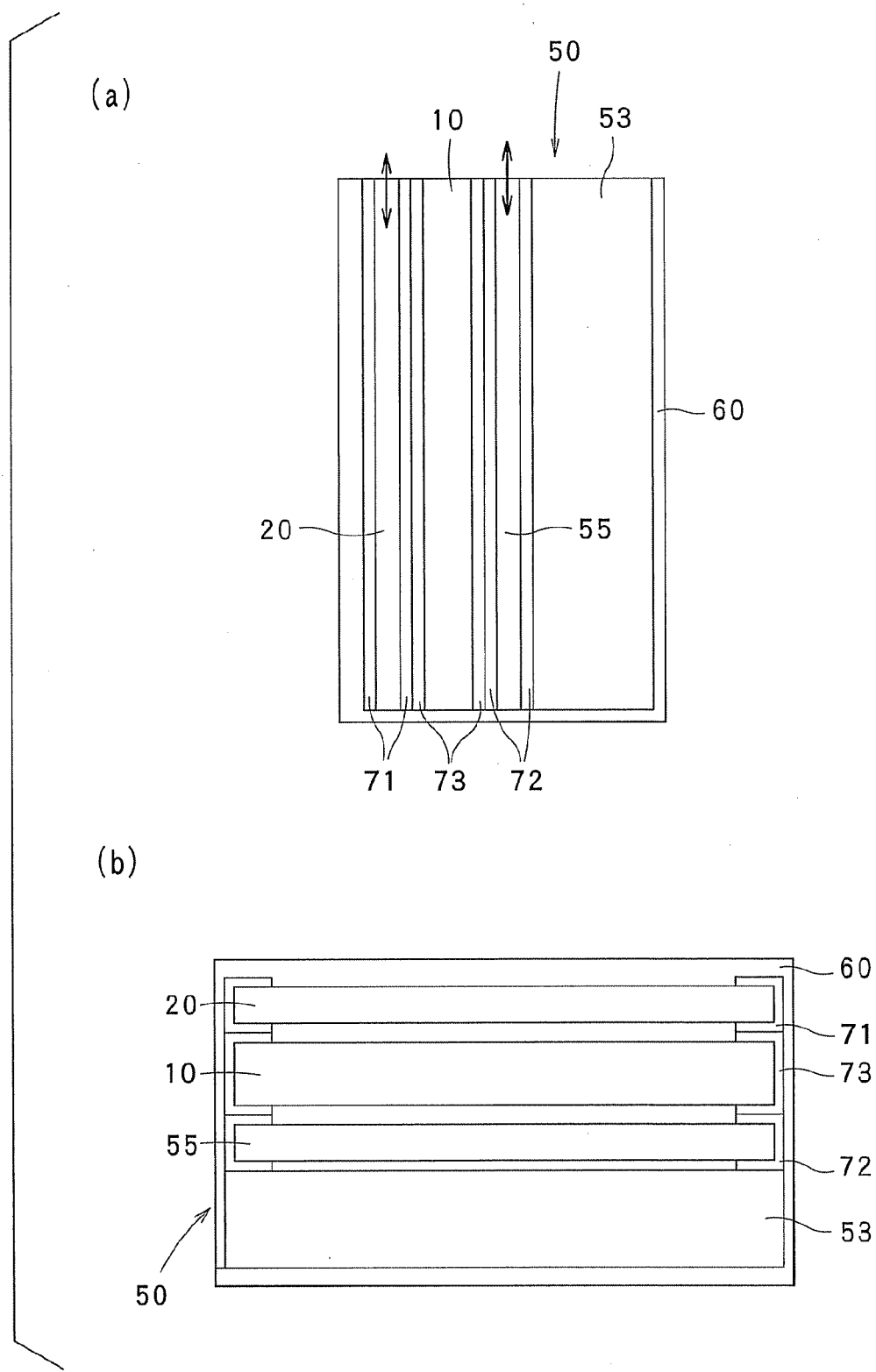
FIG. 6 is a diagrammatic sectional view showing a holder in the second embodiment of a plate inspection system according to the present invention.
Figure 7:
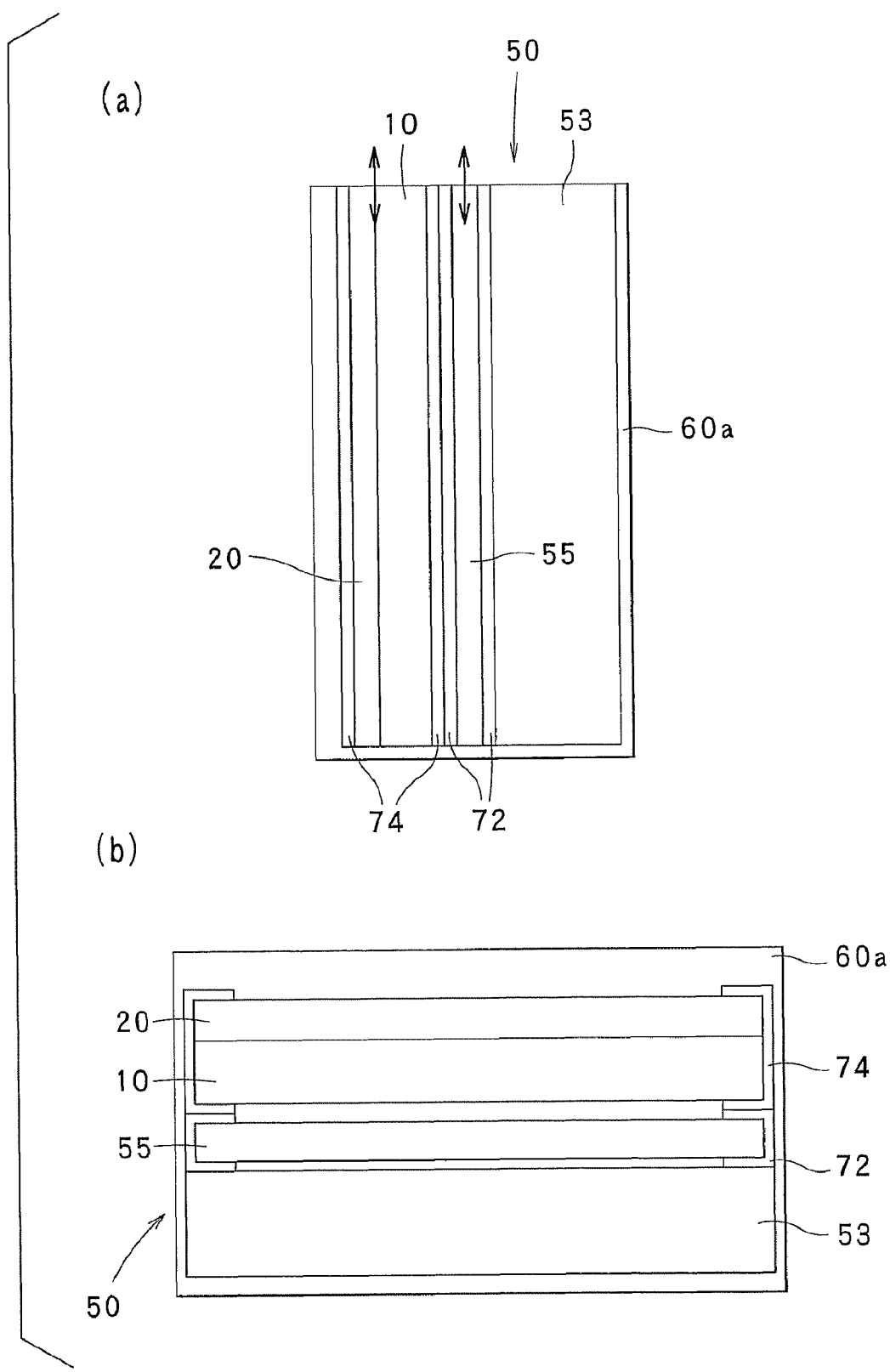
FIG. 7 is a diagrammatic sectional view showing a modification of the holder in the second embodiment of a plate inspection system according to the present invention.

Like reference characters designate corresponding parts throughout FIGS. 5 to 7 showing the second embodiment and FIGS. 1 to 4 showing the first embodiment, and these parts will not be described in detail in the following description.

Both the observation-side polarizer 20 and the light-source-side polarizer 55 are replaceable, as shown in FIGS. 6(a) and 6(b). Therefore, if observation-side polarizers 20 and light-source-side polarizers 55 that have different axes of transmission have been prepared beforehand, the observation-side polarizer 20 and the light-source-side polarizer 55 that are held by the holder 60 can be replaced with a observation-side polarizer 20 and a light-source-side polarizer 55 that have the desired axis of transmission, respectively.

It is thus possible to change freely the relationship between the direction of the axis of transmission of the observation-side polarizer 20 and that of the axis of transmission of the light-source-side polarizer 55, so that irregularities in phase difference in the color filter 10 can be effectively defected.

Such a holder 60 may also be placed on the plate mount 80 shown in the first embodiment (see FIG. 2). By placing the holder 60 on the plate mount 80, a color filter 10 can be positioned at such a point that irregularities in phase difference in the color filter 10 can be clearly recognized, so that the irregularities in phase difference can be efficiently detected.

FIGS. 6(a) and 6(b) show the example that the observation-side polarizer 20 and the color filter 10 are separated from each other. The present invention is not limited to this example, and the observation-side polarizer 20 and the color filter 10 may be united into one, as shown in FIGS. 7(a) and 7(b). In this case, the holder 60 has a fourth guide rail 74 for replaceably guiding and holding the observation-side polarizer 20 and the color filter 10 and a second guide rail 72 for replaceably guiding and holding the light-source-side polarizer 55, as shown in FIGS. 7(a) and 7(b). FIG. 7(a) is a cross-sectional view of the holder 60a holding the observation-side polarizer 20 and the color filter 10, which are united into one, and the light-source-side polarizer 55. FIG. 7(b) is a plane view of the holder 60a holding the observation-side polarizer 20 and the color filter 10, which are united into one, and the light-source-side polarizer 55.

Method of Inspecting Color Filter

Figure 8:
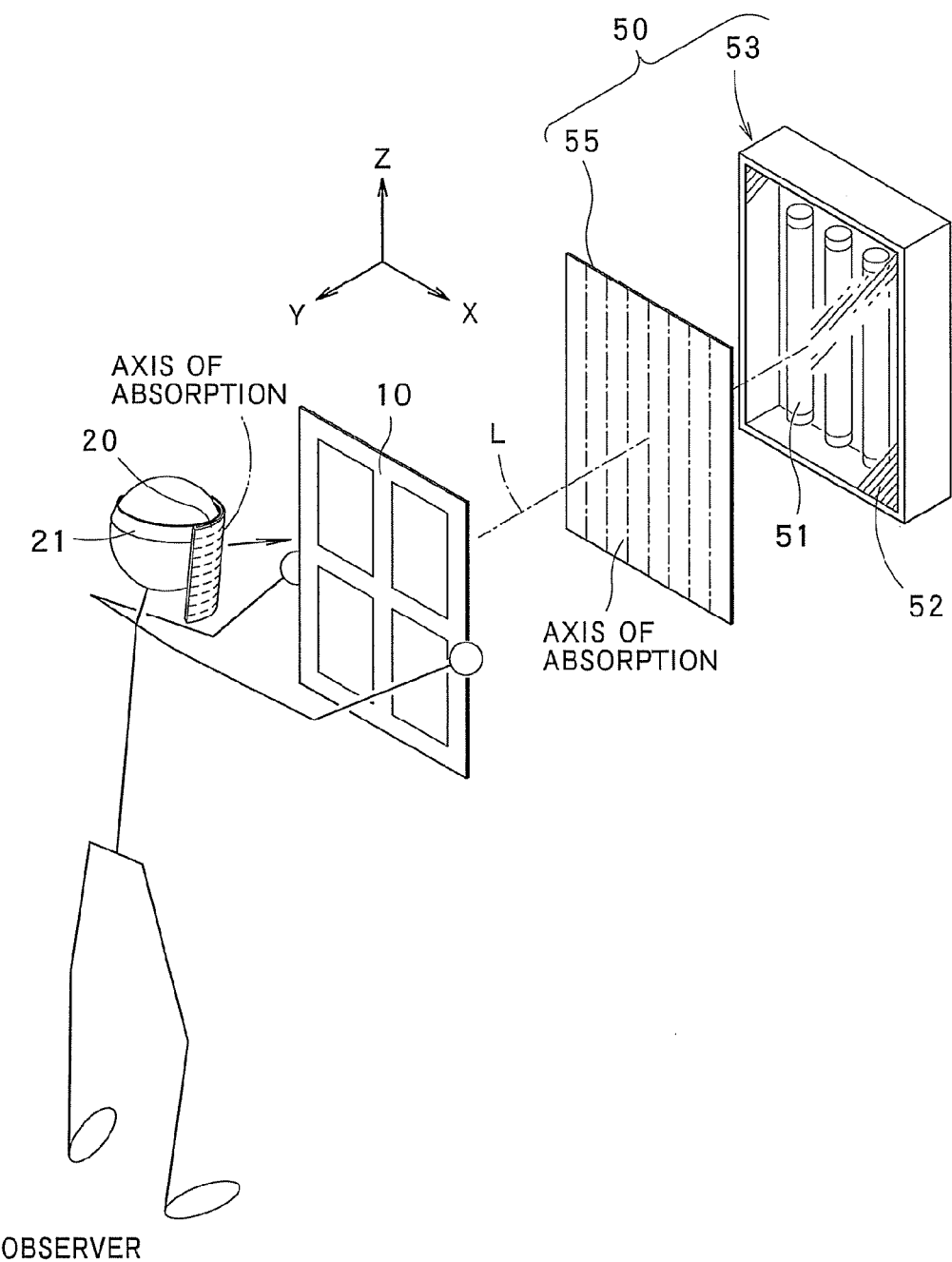
FIG. 8 is a diagrammatic view for explaining a plate inspection method according to the present invention.
Figure 9:
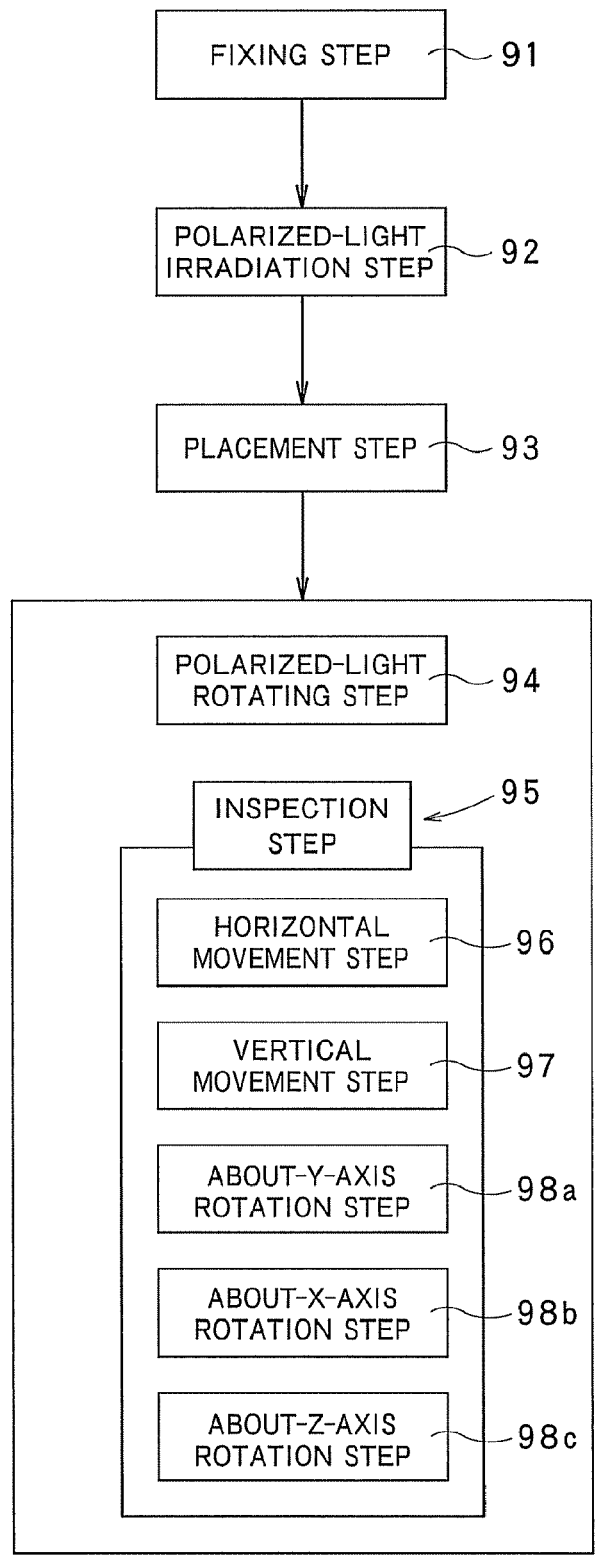
FIG. 9 is a flow chart showing the steps in the plate inspection method according to the present invention.

Next, with reference to FIGS. 8 and 9, a method of inspecting a color filter 10 for irregularities in phase difference, without using the above-described plate mount 80 and holder 60. Like reference characters designate corresponding parts throughout FIGS. 8 and 9 and FIGS. 1 to 4 showing the first embodiment, and these parts will not be described in detail in the following description.

First, an observer fixes the observer-side polarizer 20 to his/her head (the fixing step 91) (see FIGS. 8 and 9).

Next, the electric power is supplied to the polarized-light source 50 to make the polarized-light source 50 irradiate polarized light (the polarized-light irradiation step 92) (see FIGS. 8 and 9).

With his/her hand, the observer then places a color filter 10 between the polarized-light source 50 and the observation-side polarizer 20 so that it is irradiated with polarized light from the polarized-light source 50 (the placement step 93) (see FIGS. 8 and 9).

The observer inspects the color filter 10 by observing it through the observer-side polarizer 20 while changing the position of the color filter 10 relative to the polarized-light source 50 (the inspection step 95). In this step, the light-source-side polarizer 55 in the polarized-light source 50 is rotated about the axis L of rotation (the polarized-light-rotating step 94) (see FIGS. 8 and 9).

By rotating the light-source-side polarizer 55 in this manner, the axis of polarization of polarized light from the polarized-light source 50 can be changed relative to the color filter 10. Further, by changing the position of the color filter 10 relative to the polarized-light source 50, the color filter 10 can be positioned at such a point that irregularities in phase difference in the color filter 10 can be clearly recognized. These operations make it possible to detect irregularities in phase difference in the color filter 10 efficiently.

The step of inspecting the color filter 10 while changing the position of the color filter 10 relative to the polarized-light source 50 (the inspection step 95) can be carried out in the following manner: the position of the color filter 10 is changed horizontally relative to the direction to the observation side from the polarized-light source 50 (the horizontal movement step 96); the position of the color filter 10 is changed vertically relative to the direction to the observation side from the polarized-light source 50 (the vertical movement step 97); the color filter 10 is rotated about the axis extending in the direction to the observation side from the polarized-light source 50 (the about-Y-axis rotation step 98a); the color filter 10 is rotated about the horizontal axis perpendicular to the direction to the observation side from the polarized-light source 50 (the about-X-axis rotation step 98b); or the color filter 10 is rotated about the vertical axis perpendicular to the direction to the observation side from the polarized-light source 50 (the about-Z-axis rotation step 98c) (see FIGS. 8 and 9).

In the above-described embodiments and color filter inspection method, such a liquid as glycerin, water or matching oil for refractive-index matching may be poured into a space between two of the optical members (e.g., the white-light source 51, the polarized-light-source color filter 52, the light-source-side polarizer 55, the color filter 10, the observation-side polarizer 20, etc.). This is because, since surface reflection occurring at each interface can be canceled by matching refractive indexes, the inspection of a color filter for irregularities in phase difference can be performed more accurately.

Third Embodiment

Figure 10:
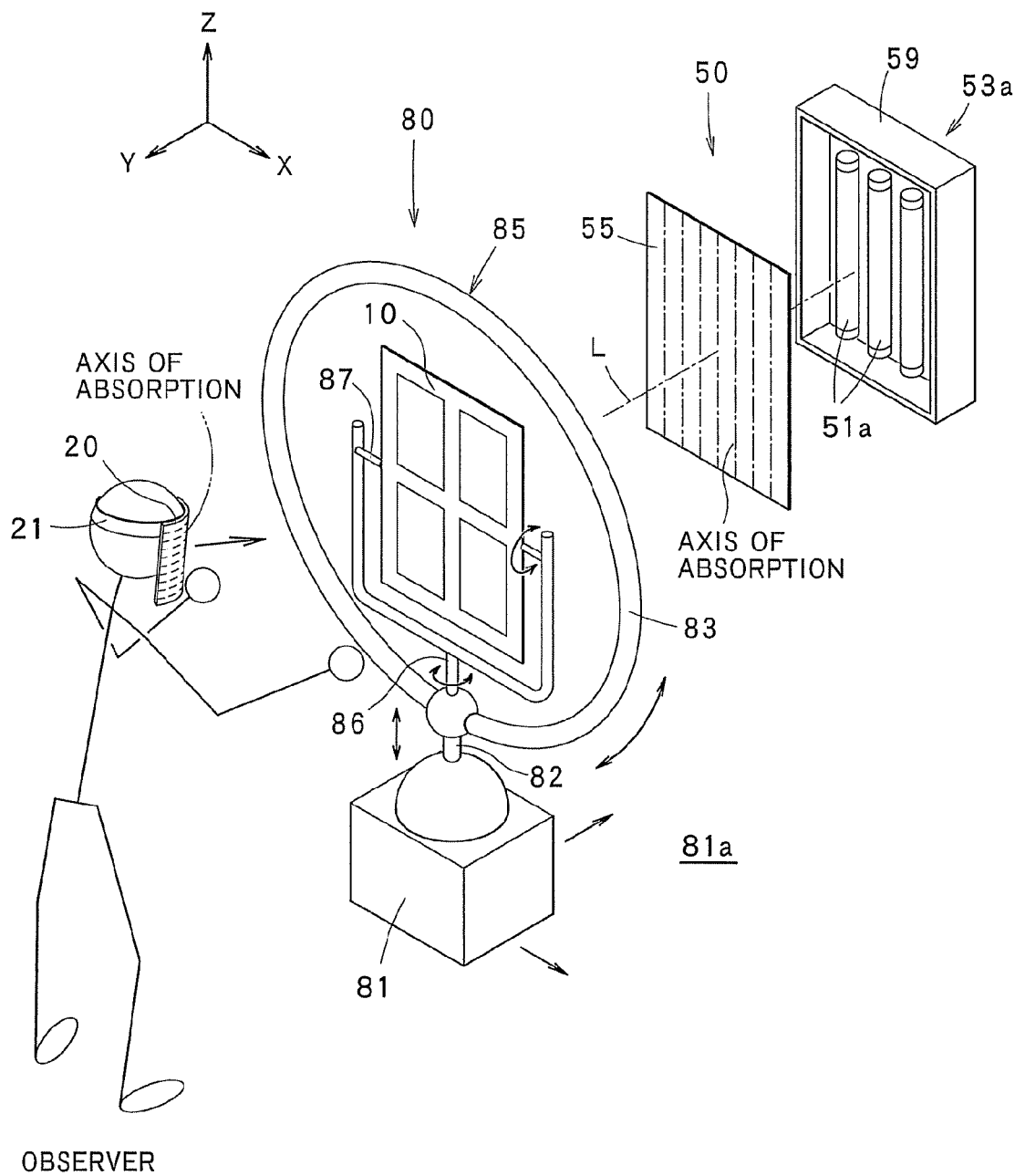
FIG. 10 is a diagrammatic view showing the third embodiment of a plate inspection system according to the present invention.
Figure 11:
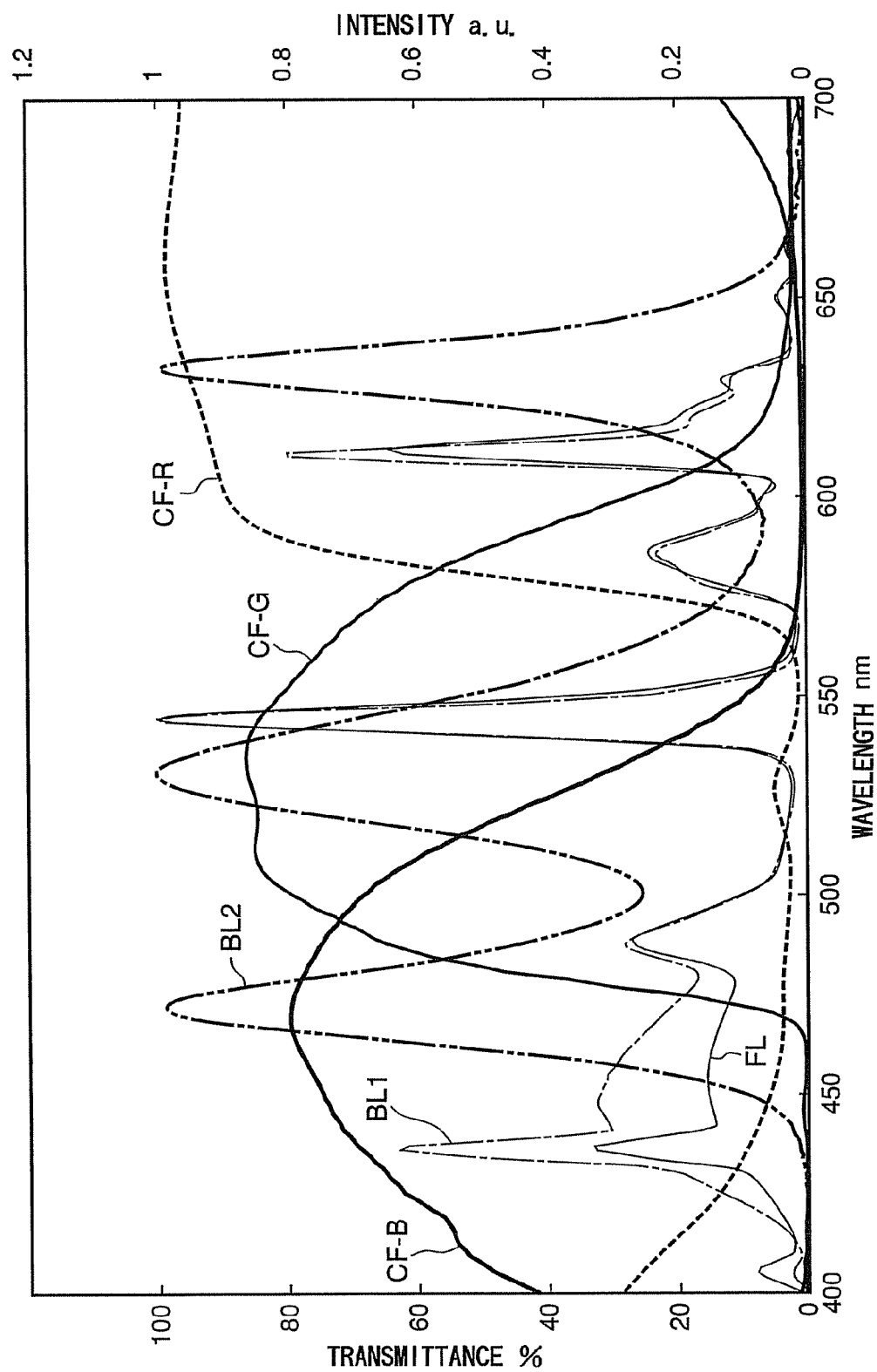
FIG. 11 is graphs showing the relationship between the wavelength of light from a backlight lamp and the intensity of the light, and the relationship between the wavelength of light passing through color pixels in a color filter and the transmittance of the light, obtained in the third embodiment of a plate inspection system according to the present invention.

Next, the third embodiment of the present invention will be described with reference to FIGS. 10 and 11. The third embodiment shown in FIGS. 10 and 11 is that a light source 53a having backlight lamps 51a that irradiate light having wavelengths substantially the same as the wavelengths at which the transmittances of light passing through red pixels 2a, green pixels 2b and blue pixels 2c in a color filter 10 reach a maximum is used instead of the light source 53 having the white-light source 51 and the polarized-light-source color filter 52 placed on the color filter 10 side of the white-light source 51. Except for this point, the third embodiment is almost the same as the first embodiment shown in FIGS. 1 to 4. The backlight lamps 51a are red, green and blue LEDs (light-emitting diodes), CCFLs (cold cathode fluorescent lamps), or the like. FIG. 11 is graphs showing the relationship between the wavelength of light from the backlight lamps 51a and the intensity of the light, and the relationship between the wavelength of light passing through the color pixels 2a, 2b, or 2c in the color filter 10 and the transmittance of the light.

Like reference characters designate corresponding parts throughout FIGS. 10 and 11 showing the third embodiment and FIGS. 1 to 4 showing the first embodiment, and these parts will not be described in detail in the following description.

In FIG. 10, the light source 53a in the polarized-light source 50 of this embodiment has the backlight lamps 51a that irradiate light having wavelengths substantially the same as the wavelengths at which the transmittances of light passing through the red pixels 2a, green pixels 2b and blue pixels 2c in the color filter 10 reach a maximum (see FIG. 1). Therefore, polarized light from the polarized-light source 50 efficiently pass through the color pixels 2a, 2b, 2c in the color filter 10, so that an observer can more efficiently detect irregularities in phase difference in the color filter 10. The light source 53a has a frame 59 for holding the backlight lamps 51a.

The light having wavelengths substantially the same as the wavelengths at which the transmittances of light passing through the color pixels 2a, 2b, 2c in the color filter 10 reach a maximum herein refers to light having intensity peaks in wavelength ranges between wavelengths at which the transmittances of light passing through the color pixels 2a, 2b, 2c reach a maximum and wavelengths at which the transmittances of the light are 60% of the peak transmittances (as for the light passing through the red pixels 2a, the peak transmittance observed at a wavelength in the vicinity of 650 mm).

For example, in FIG. 11, light having wavelengths substantially the same as the wavelengths at which the transmittances of light passing through the color pixels 2a, 2b, 2c reach a maximum refers to the light passing through the blue pixels 2c, having an intensity peak in the range of about 405 nm to about 520 nm, the light passing through the green pixels 2b, having an intensity peak in the range of about 485 nm to about 585 nm, and the light passing through the red pixels 2a, having an intensity peak in the range of about 585 nm to about 700 nm, the longer-wavelength-side end of the visible light range.

In FIG. 11, curve BL1 shows the relationship between the wavelength and intensity of light from CCFLs (cold cathode fluorescent lamps), and curve BL2 shows the relationship between the wavelength and intensity of light from red, green, and blue LEDs (light-emitting diodes). Further, in FIG. 11, curve CF-R shows the relationship between the wavelength and transmittance of the light passing through the red pixels 2a, curve CF-G shows the relationship between the wavelength and transmittance of the light passing through the green pixels 2b, and curve CF-B shows the relationship between the wavelength and transmittance of the light passing through the blue pixels 2c. In FIG. 11, curve FL shows the relationship between the wavelength and intensity of light from an ordinary fluorescent lamp.

In FIG. 10, the color temperature of the light from the backlight lamps 51a is preferably 7,000 K or more, more preferably 10,000 K or more.

When the color temperature of the light from the backlight lamps 51a is 7,000 K or more, the influence, on the polarized light, of those members (yellowish members) around the polarized light, such as the frame 59 in the polarized-light source 50, can be cancelled. Therefore, the polarized light can pass through the blue pixels in the color filter 10 in a sufficiently great amount, as compared with light from an ordinary fluorescent lamp. An observer can thus more efficiently detect irregularities in phase difference in the color filter 10.

On the other hand, when the color temperature becomes excessively high, the amount of the light that has passed through the blue pixels becomes too great, as compared with the amounts of the light that have passed through the green and red pixels, so that it becomes relatively difficult to view irregularities in phase difference caused at the green and red pixels. It is therefore preferred that the color temperature of the light from the backlight lamps 51a be 30,000 K or less.

The color temperature of light from a conventional fluorescent lamp is 6,700 K.

The invention claimed is:

1. A plate inspection system for use in the inspection of a plate having a retardation layer, comprising:
   a polarized-light source for irradiating a polarized light, and
   an observation-side polarizer placed on the observation side,
   wherein a plate to be inspected is placed between the polarized-light source and the observation-side polarizer so that the plate to be inspected is irradiated with the polarized light from the polarized-light source and the polarized light passes through the plate to be inspected and is observed through the observation-side polarizer, and the plate to be inspected is rotatable about at least one axis that extends perpendicular to a direction extending from the polarized-light source to the observation side.

2. The plate inspection system according to claim 1, wherein the observation-side polarizer or the plate to be inspected is movable in the horizontal direction relative to the polarized-light source.

3. The plate inspection system according to claim 1, wherein the observation-side polarizer or the plate to be inspected is movable in the vertical direction relative to the polarized-light source.

4. The plate inspection system according to claim 1, wherein the observation-side polarizer is rotatable relative to the polarized-light source.

5. The plate inspection system according to claim 1, wherein the polarized-light source is movable in the horizontal direction relative to the observation-side polarizer or the plate to be inspected.

6. The plate inspection system according to claim 1, wherein the polarized-light source is movable in the vertical direction relative to the observation-side polarizer or the plate to be inspected.

7. The plate inspection system according to claim 1, wherein the polarized-light source is, relative to the observation-side polarizer or the plate to be inspected, rotatable about the axis extending in the direction to the observation side from the polarized-light source, the horizontal axis perpendicular to the direction to the observation side from the polarized-light source, and/or the vertical axis perpendicular to the direction to the observation side from the polarized-light source.

8. The plate inspection system according to claim 1, wherein the plate to be inspected is a color filter having a retardation layer.

9. The plate inspection system according to claim 8, wherein the polarized-light source irradiates polarized light colored in one of the three colors, red (R), green (G), and blue (B).

10. The plate inspection system according to claim 9, wherein the polarized-light source has a white-light source and a polarized-light-source color filter colored in one of the three colors R, G, and B, placed on the plate to be inspected side of the white-light source, and irradiates polarized light colored in one of the three colors, R, G, and B owing to coloring white light from the white-light source by the polarized-light color filter.

11. The plate inspection system according to claim 10, wherein the plate to be inspected is a color filter having multiple red, green and blue pixels, the dominant wavelength of light colored in red by the polarized-light-source color filter in the polarized-light source is substantially the same as the dominant wavelength of the red color of the red pixels in the color filter that is the plate to be inspected, the dominant wavelength of light colored in green by the polarized-light-source color filter in the polarized-light source is substantially the same as the dominant wavelength of the green color of the green pixels in the color filter, and the dominant wavelength of light colored in blue by the polarized-light-source color filter in the polarized-light source is substantially the same as the dominant wavelength of the blue color of the blue pixels in the color filter.

12. The plate inspection system according to claim 8, wherein the polarized-light source has a source of red light, a source of green light, and a source of blue light, and the three color-light sources are independently switched on or off.

13. The plate inspection system according to claim 12, wherein the color-light sources in the polarized-light source are cold cathode fluorescent tubes or LEDs.

14. The inspection system according to claim 8, wherein the color filter has color pixels of at least one of red, green and blue, and the polarized-light source irradiates polarized light having a wavelength substantially the same as the wavelength at which the transmittance of light passing through the color pixels reaches a maximum.

15. The inspection system according to claim 14, wherein the color filter has red, green, and blue pixels, and the polarized-light source irradiates polarized light having wavelengths substantially the same as the wavelengths at which the transmittances of light passing through the red, green, and blue pixels reach a maximum.

16. The inspection system according to claim 15, wherein the polarized-light source has LEDs or CCFLs that irradiate light having wavelengths substantially the same as the wavelengths at which the transmittances of light passing through the red, green, and blue pixels reach a maximum.

17. The plate inspection system according to claim 1, wherein the polarized-light source comprises a light source and a light-source-side polarizer placed on the plate to be inspected side of the light source.

18. The plate inspection system according to claim 17, wherein the light-source-side polarizer in the polarized-light source is rotatable about the normal to the light-source-side polarizer, the axis of rotation.

19. The plate inspection system according to claim 17, further comprising a light-source-side-polarizer holder for replaceably holding the light-source-side polarizer, wherein the light-source-side polarizer held by the light-source-side-polarizer holder is replaceable with another light-source-side polarizer having the desired axis of transmission.

20. The plate inspection system according to claim 1, wherein the intensity of light from the polarized-light source is adjustable.

21. The plate inspection system according to claim 1, wherein the observation-side polarizer is fixable to the observer's head.

22. The plate inspection system according to claim 21, wherein the observation-side polarizer is combined with a holding frame for fixing the observation-side polarizer to the observer's head.

23. The plate inspection system according to claim 22, wherein the observation-side polarizer is rotatable about the normal to the observation-side polarizer, the axis of rotation, owing to a screw mechanism made in the holding frame.

24. The plate inspection system according to claim 1, further comprising an observation-side-polarizer holder for replaceably holding the observation-side polarizer, wherein the observation-side polarizer held by the observation-side-polarizer holder is replaceable with another observation-side polarizer having the desired axis of transmission.

25. The plate inspection system according to claim 1, further comprising a plate mount for holding the plate to be inspected, wherein the position of the plate to be inspected relative to the polarized-light source is changed by the plate mount.

26. The plate inspection system according to claim 25, wherein the plate mount has a horizontally movable part that can be moved in the horizontal direction relative to the plate to be inspected, and a rotary part for holding and rotating the plate to be inspected, placed on the horizontally movable part.

27. The plate inspection system according to claim 26, wherein the rotary part has an about-Y-axis rotary part that rotates the plate to be inspected about the axis extending in the direction to the observation side from the polarized-light source, an about-X-axis rotary part that rotates the plate to be inspected about the horizontal axis perpendicular to the direction to the observation side from the polarized-light source, and an about-Z-axis rotary part that rotates the plate to be inspected about the vertical axis perpendicular to the direction to the observation side from the polarized-light source.

28. The plate inspection system according to claim 26, wherein the plate mount further has, between the horizontally movable part and the rotary part, a vertically extendable part that can be vertically elongated.

29. A plate inspection method for inspecting a plate by the use of an inspection system for use in the inspection of a plate having a retardation layer, comprising a polarized-light source for irradiating a polarized light and an observation-side polarizer placed on the observation side, the method comprising:

a placement step of placing a plate to be inspected between the polarized-light source and the observation-side polarizer so that the plate to be inspected is irradiated with polarized light from the polarized-light source, and an inspection step of inspecting the plate to be inspected by observing the polarized light which has passed through the plate to be inspected through the observation-side polarizer while rotating the plate to be inspected about at least one axis that extends perpendicular to a direction extending from the polarized-light source to the observation side.

30. The plate inspection method according to claim 29, in which the inspection step comprises at least one of the following steps: a horizontal movement step of horizontally moving the position of the plate to be inspected relative to the polarized-light source, a vertical movement step of vertically moving the position of the plate to be inspected relative to the polarized-light source, a about-Y-axis rotation step of rotating the plate to be inspected about the axis extending in the direction to the observation side from the polarized-light source, a about-X-axis rotation step of rotating the plate to be inspected about the horizontal axis perpendicular to the direction to the observation side from the polarized-light source, and a about-Z-axis rotation step of rotating the plate to be inspected about the vertical axis perpendicular to the direction to the observation side from the polarized-light source.

31. A plate inspection method for inspecting a plate by the use of an inspection system for use in the inspection of a plate composed of a color filter having a retardation layer and color pixels of at least one of red, green and blue, the system comprising a polarized-light source for irradiating a polarized light and an observation-side polarizer placed on the observation side, the method comprising:

a placement step of placing a plate to be inspected between the polarized-light source and the observation-side polarizer so that the plate to be inspected is irradiated with polarized light from the polarized-light source, and an inspection step of inspecting the plate to be inspected by observing the polarized light which has passed through the plate to be inspected through the observation-side polarizer while rotating the plate to be inspected about at least one axis that extends perpendicular to a direction extending from the polarized-light source to the observation side, wherein the wavelength of the polarized light from the polarized-light source is substantially the same as the wavelength at which the transmittance of light passing through the color pixels reaches a maximum.

* * * * *